United States Patent [19]

Ahr et al.

[11] Patent Number: 5,460,624
[45] Date of Patent: Oct. 24, 1995

[54] SANITARY NAPKIN

[75] Inventors: Nick A. Ahr; Michael E. Carrier, both of Cincinnati, Ohio

[73] Assignee: The Procter & Gamble Company, Cincinnati, Ohio

[21] Appl. No.: 236,607

[22] Filed: May 2, 1994

[51] Int. Cl.⁶ .............................. A61F 13/15; A61F 13/20
[52] U.S. Cl. .................. 604/385.1; 604/358; 604/386; 604/387; 428/198
[58] Field of Search .................................. 604/358, 378, 604/383, 385.1, 386, 387, 389–390, 393, 395; 602/57–59; 428/198

[56] References Cited

U.S. PATENT DOCUMENTS

| | | |
|---|---|---|
| 2,929,379 | 3/1960 | Poulsen . |
| 3,367,334 | 2/1968 | Testa . |
| 3,397,697 | 8/1968 | Rickard . |
| 3,570,492 | 3/1971 | Bettencourt . |
| 3,913,580 | 10/1975 | Ginocchio . |
| 4,186,743 | 2/1980 | Steiger . |
| 4,285,343 | 8/1981 | McNair . |
| 4,405,310 | 9/1983 | Karami . |
| 4,425,130 | 1/1984 | DesMarais . |
| 4,505,707 | 3/1985 | Feeney ........................ 604/387 |
| 4,536,181 | 8/1985 | Cook . |
| 4,576,597 | 3/1986 | Hlaban . |
| 4,589,876 | 5/1986 | Van Tilburg . |
| 4,596,570 | 6/1986 | Jackson et al. . |
| 4,597,759 | 7/1986 | Johnson . |
| 4,701,178 | 10/1987 | Glaug et al. . |
| 4,759,754 | 7/1988 | Korpman . |
| 4,773,905 | 9/1988 | Molee et al. . |
| 4,938,756 | 7/1990 | Salek ........................ 604/378 |
| 4,964,857 | 10/1990 | Osborn ...................... 604/358 |
| 5,009,653 | 4/1991 | Osborn, III . |
| 5,057,096 | 10/1991 | Faglione .................... 604/358 |
| 5,125,918 | 6/1992 | Seidy . |
| 5,133,704 | 7/1992 | Wheeler . |
| 5,133,705 | 7/1992 | Nakanishi et al. . |
| 5,201,727 | 4/1993 | Nakanishi et al. . |
| 5,221,275 | 6/1993 | Van Iten . |
| 5,275,591 | 1/1994 | Mavinkurve . |
| 5,281,209 | 1/1994 | Osborn, III . |
| 5,295,988 | 3/1994 | Muckenfuhs et al. ........ 604/358 |
| 5,328,450 | 7/1994 | Smith et al. ................ 604/378 |

FOREIGN PATENT DOCUMENTS

| | | |
|---|---|---|
| 2374890 | 12/1976 | France . |
| WO92/18080 | 10/1992 | WIPO . |

Primary Examiner—Randall L. Green
Assistant Examiner—P. Zuttarelli
Attorney, Agent, or Firm—William Scott Andes; E. Kelly Linman; Jacobus C. Rasser

[57] ABSTRACT

The present invention pertains to a sanitary napkin. The sanitary napkin includes a topsheet, a first backsheet joined to the topsheet, and an absorbent core positioned between the topsheet and the first backsheet. A second backsheet is joined to the first backsheet. The second backsheet includes a line of weakness defining a portion of the second backsheet to be separated from the remainder of the second backsheet. The second backsheet is secured to the first backsheet within the line of weakness along a plurality of bond sites. The bond sites form perforations in the first backsheet upon separation and removal of the second backsheet within the line of weakness.

10 Claims, 2 Drawing Sheets 5,460,624

SANITARY NAPKIN

TECHNICAL FIELD

The present invention relates to a sanitary napkin, and more particularly, the present invention relates to a sanitary napkin having a second backsheet of which all or a portion thereof may be separated from a first backsheet such that the sanitary napkin may be secured to another sanitary napkin to provide additional absorptive capacity.

BACKGROUND OF THE INVENTION

Sanitary napkins configured for the absorption of bodily fluids are, of course, well-known. In their simplest form they comprise an absorbent element or core o interposed between a liquid pervious body contacting element and a liquid impervious protective barrier. The absorbent element is, of course, intended to receive and contain menses and other vaginal discharges. The body contacting element (sometimes called a topsheet) is intended to provide more or less comfortable and dry-feeling contact with body surfaces while allowing free passage of fluids therethrough and into the absorbent as core. The protective barrier (sometimes called a backsheet) is intended to prevent menses or other vaginal discharges which are expelled or escape from the absorbent core from soiling the user's undergarments.

In addition to the three functional elements mentioned above, sanitary napkins are generally provided with means for supporting the device adjacent the user's crotch area, even as the user moves, where it can most effectively perform its intended function. Traditionally, this support means has involved the use of waist encircling belts having suspenders depending from the front and rear thereof. The suspenders are of various designs and are provided with means of various designs for securing the sanitary napkin thereto.

More recently, sanitary napkins have been provided with an adhesive attachment means for securing the sanitary napkin to the crotch area of the user's undergarment. Elimination of the traditional belt is generally considered to be a definite advance in sanitary napkin technology.

While prior art sanitary napkins do perform their intended function, they are limited to the amount of fluid they can absorb by the capacity of the absorbent element.

SUMMARY OF THE INVENTION

The present invention pertains, in a preferred embodiment, to a sanitary napkin including a topsheet, a first backsheet joined to said topsheet, and an absorbent core positioned between said topsheet and said first backsheet. The absorbent article comprises a second backsheet joined to the exterior or garment facing surface of said first backsheet. The second backsheet includes a line of weakness defining a portion of said second backsheet to be separated from the remainder of said second backsheet. The second backsheet is secured to said first backsheet within said line of weakness. Preferably, the second backsheet is secured to the first backsheet within said line of weakness along a plurality of bond sites. Upon separation of the portion of said second backsheet within the lines of weakness a plurality of apertures are formed in the first backsheet.

The line of weakness is preferably substantially continuous. The line of weakness may include perforations.

The exposed or garment facing surface of the second backsheet preferably includes an adhesive fastening means. A removable release liner preferably covers said adhesive fastening means.

BRIEF DESCRIPTION OF THE DRAWINGS

While the specification concludes with claims particularly pointing out and distinctly claiming the present invention, it is believed that the present invention will be better understood from the following description in conjunction with the accompanying drawings, in which like reference numbers identify identical elements and wherein:

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use, and, preferably, to be recycled, composted or otherwise disposed of in an environmentally compatible manner). A "unitary" absorbent article refers to absorbent articles which are formed of separate parts united together to form a coordinated entity so that they do not require separate manipulative pans like a separate holder and pad.

Figure 1:
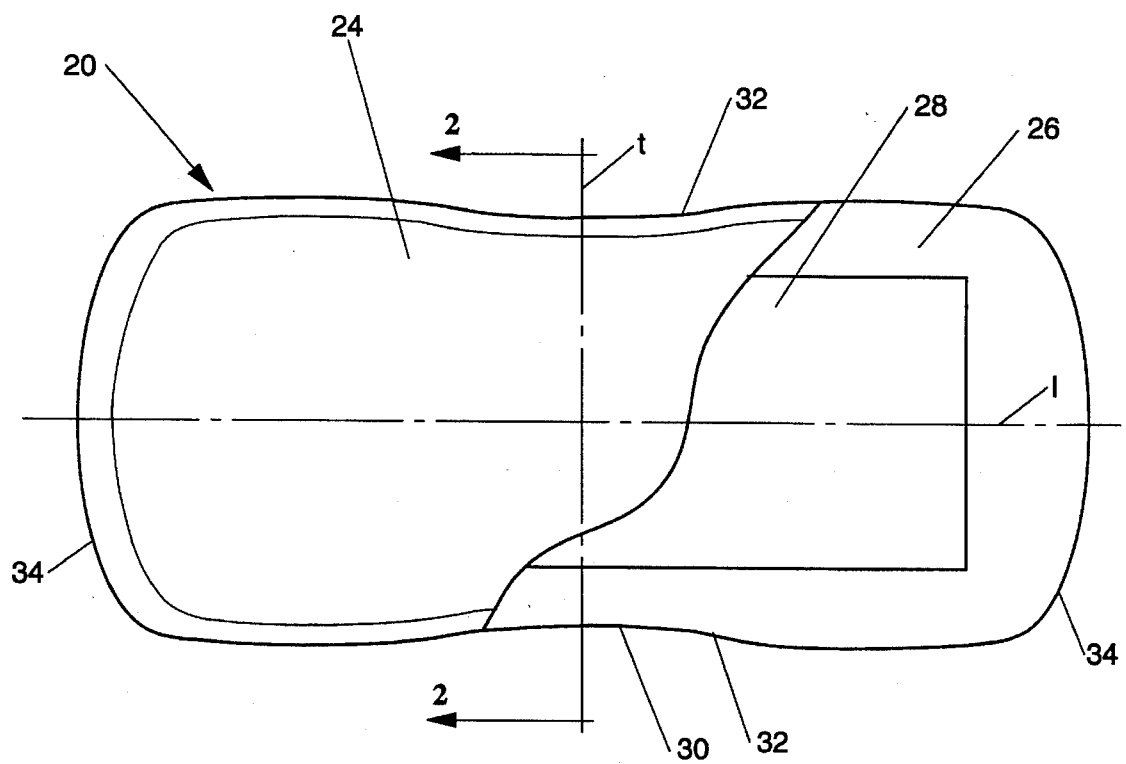
FIG. 1 is a top plan view of a sanitary napkin embodiment of the present invention with portions of the sanitary napkin cut-away to more clearly show the construction of the sanitary napkin and with the portion of the sanitary napkin which faces or contracts the wearer, oriented towards the viewer.

A preferred embodiment of a unitary disposable absorbent article of the present invention is the catamenial pad, sanitary napkin 20, shown in FIG. 1. As used herein, the term "sanitary napkin" refers to an absorbent article which is worn by females adjacent to the pudendal region, generally external to the urogenital region, and which is intended to absorb and contain menstrual fluids and other vaginal discharges from the wearer's body (e.g., blood, menses, and urine). Interlabial devices which reside partially within and partially external of the wearer's vestibule are also within the scope of this invention. As used herein, the term "pudendal" refers to the externally visible female genitalia. It should be understood, however, that the present invention is also applicable to other feminine hygiene or catamenial pads such as pantiliners, or other absorbent articles such as incontinence pads, and the like.

FIG. 1 is a plan view of the sanitary napkin 20 of the present invention in its flat-out state with portions of the structure being cut-away to more clearly show the construction of the sanitary napkin 20 and with the portion of the sanitary napkin 20 which faces or contacts the wearer, oriented towards the viewer. As shown in FIG. 1, the sanitary napkin 20 preferably comprises a liquid pervious topsheet 24, a first liquid impervious backsheet 26 joined with the topsheet 24, an absorbent core 28 positioned between the topsheet 24 and the first backsheet 26, and a second liquid impervious backsheet 29 (shown in FIG. 2) secured to the first backsheet 26.

The sanitary napkin 20 has two surfaces, a body-contacting surface, body facing surface, or "body surface" and a garment facing surface, or garment surface. The sanitary napkin 20 is shown in FIG. 1 as viewed from its body surface. The body surface is intended to be worn adjacent to the body of the wearer while the garment surface is on the opposite side and is intended to be placed adjacent to the wearer's undergarments when the sanitary napkin 20 is worn.

The sanitary napkin 20 has two centerlines, a longitudinal centerline "1" and a transverse centerline "t". The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral" as used herein, are interchangeable, and refer to a line, axis or direction which lies within the plane of the sanitary napkin 20 that is generally perpendicular to the longitudinal direction. FIG. 1 also shows that the sanitary napkin 20 has a periphery 30 which is defined by the outer edges of the sanitary napkin 20 in which the longitudinal edges are designated 32 and the end edges are designated 34.

FIG. 1 shows a preferred embodiment of the sanitary napkin 20 in which the topsheet 24 and the first backsheet 26 have length and width dimensions generally larger than those of the absorbent core 28. The topsheet 24 and the first backsheet 26 extend beyond the edges of the absorbent core 28 to thereby form portions of the periphery 30.

Figure 2:
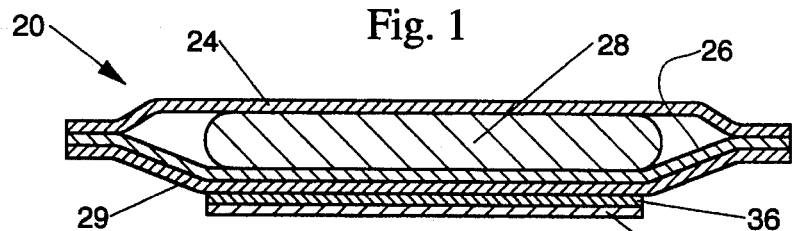
FIG. 2 is a cross-sectional view of the sanitary napkin of FIG. 1 taken along section line 2—2.

FIG. 2 is a cross-sectional view of the sanitary napkin 20 taken along section line 2—2 of FIG. 1. As can be seen in FIG. 2 the sanitary napkin 20 preferably includes an adhesive fastening means 36 on the exposed surface of the second backsheet 29 for attaching the sanitary napkin 20 to the undergarment of the wearer. Removable release liner 37 covers the adhesive fastening means 36 to keep the adhesive from sticking to a surface other than the crotch portion of the undergarment prior to use.

The absorbent core 28 may be any absorbent means which is capable of o absorbing or retaining liquids (e.g., menses and/or urine). As shown in FIG. 1, the absorbent core 28 has a body surface, a garment surface, side edges, and pad edges. The absorbent core 28 may be manufactured in a wide variety of sizes and shapes (e.g., rectangular, oval, hourglass, dog bone, asymmetric, etc.) and from a wide variety of liquid-absorbent materials commonly used in sanitary napkins and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these. The configuration and construction of the absorbent core may also be varied (e.g., the absorbent core may have varying caliper zones (e.g., profiled so as to be thicker in the center), hydrophilic gradients, superabsorbent gradients, or lower density and lower average basis weight acquisition zones; or may comprise one or more layers or structures). The total absorbent capacity of the absorbent core should, however, be compatible with the design loading and the intended use of the sanitary napkin. Further, the size and absorbent capacity of the absorbent core may be varied to accommodate different uses such as incontinence pads, pantiliners, regular sanitary napkins, or overnight sanitary napkins.

Exemplary absorbent structures for use as the absorbent core of the present invention are described in U.S. Pat. No. 4,950,264 issued to Osborn on Aug. 21, 1990; U.S. Pat. No. 4,610,678 issued to Weisman et al. on Sep. 9, 1986; U.S. Pat. No. 4,834,735 issued to Alemany et al. on May 30, 1989; and European Patent Application No. 0 198 683, The Procter & Gamble Company, published Oct. 22, 1986 in the name of Duenk, et at. Each of these patents are incorporated herein by reference.

The first backsheet 26 and the topsheet 24 are positioned adjacent the garment surface and the body surface, respectively, of the absorbent core 28 and are preferably joined thereto and to each other by attachment means (not shown) such as those well known in the art. For example, the first backsheet 26 and/or the topsheet 24 may be secured to the absorbent core 28 or to each other by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. under the designation HL-1258 or H-2031. The attachment means will preferably comprise an open pattern network of filaments of adhesive as is disclosed in U.S. Pat. No. 4,573,986 issued to Minetola, et al. on Mar. 4, 1986, and which is incorporated herein by reference. An exemplary attachment means of an open pattern network of filaments comprises several lines of adhesive filaments swirled into a spiral pattern such as illustrated by the apparatus and method shown in U.S. Pat. No. 3,911,173 issued to Sprague, Jr. on Oct. 7, 1975; U.S. Pat. No. 4,785,996 issued to Zieker, et at. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The first backsheet 26 and the second backsheet 29 are impervious to liquids (e.g., menses and/or urine) and are preferably manufactured from a thin plastic film, although other flexible liquid impervious materials may also be used. As used herein, the term "flexible" refers to materials which are compliant and will readily conform to the general shape and contours of the human body. The backsheets prevent the exudates absorbed and contained in the absorbent core 28 from wetting articles which contact the sanitary napkin 20 such as pants, pajamas and undergarments. The backsheets may thus comprise a woven or nonwoven material, polymeric films such as thermoplastic films of polyethylene or polypropylene, or composite materials such as a film-coated nonwoven material. Preferably, each backsheet is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-0401 and by Ethyl Corporation, Visqueen Division, of Terre Haute, Ind., under the designation XP-39385. The backsheets are preferably embossed and/or matte finished to provide a more clothlike appearance. Further, the backsheets may permit vapors to escape from the absorbent core 28 (i.e., breathable) while still preventing exudates from passing through the backsheets.

Figure 3:
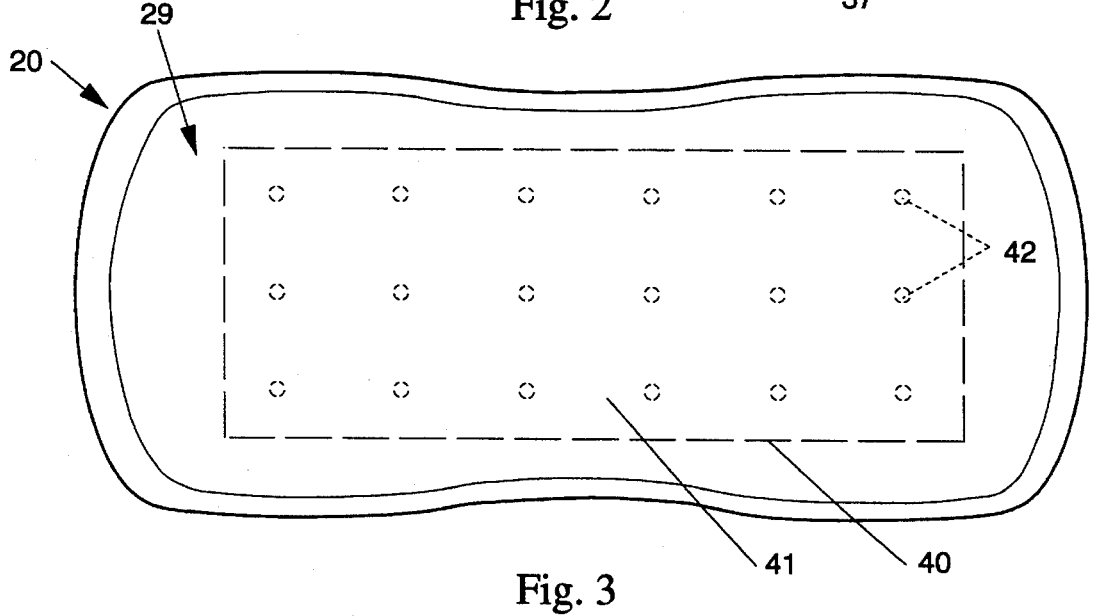
FIG. 3 is a plan view of the sanitary napkin of FIG. 1 with the portion of the sanitary napkin which faces away from the wearer oriented towards the viewer and with the fastening means and release liners removed to more clearly show the second backsheet.

FIG. 3 is a plan view of the sanitary napkin 20 of the present invention with the portion of the sanitary napkin 20 which faces away from the wearer, oriented towards the viewer and with the fastening means 36 and the release liners 37 removed to more clearly show the second backsheet 29. Second backsheet 29 includes a substantially continuous line of weakness 40 which defines at least a portion of the second backsheet indicated as 41 which may be separated from the remainder of the second backsheet 29. Second backsheet 29 is secured to first backsheet 26 along a plurality of bond sites 42. The second backsheet 29 may be secured to first backsheet 26 along bond sites 42 by any bonding means known in the art such as ultrasonic bonding, heat bonding, or by use of an adhesive. The bond sites 42 may be any size or shape, e.g., circular, oval, triangular, rectangular, square, etc.

Figure 4:
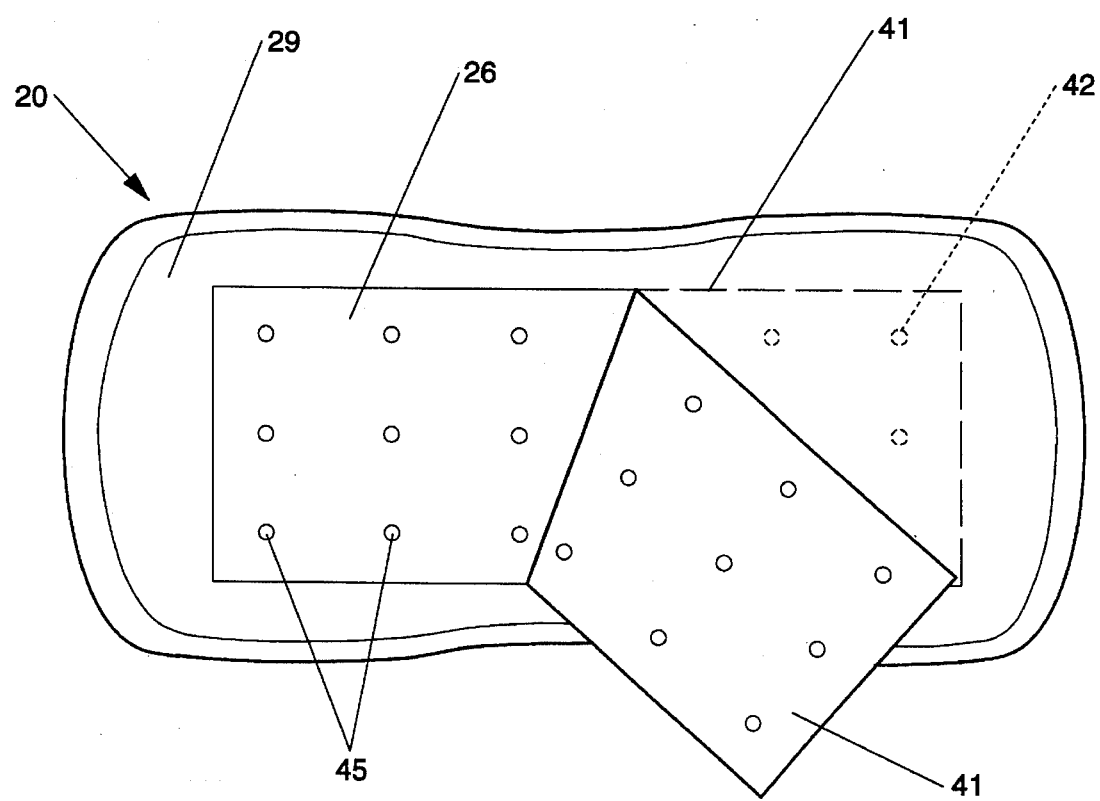
FIG. 4 is a plan view of the sanitary napkin of FIG. 3 with the portion of the second backsheet within the line, of weakness partially separated from the remainder of the second backsheet.

FIG. 4 shows the sanitary napkin 20 with the portion 41 of second backsheet 29 within the line of weakness 40 partially separated from the remainder of second backsheet 29 such that a portion of first backsheet 26 is exposed. Upon separation of backsheet portion 41 a plurality of apertures 45 are created in the first backsheet 26 at locations corresponding to bond sites 42.

First backsheet 26 preferably includes an adhesive (not shown) such that after the portion of the second backsheet 29 has been removed, the sanitary napkin 20 may be secured to another sanitary napkin to provide additional absorptive capacity. On light flow days, the sanitary napkin 20 may be used as shown in FIGS. 1–2 and may be secured to the user's undergarments or panty by adhesive fastening means 36. However, on days of heavy flow it may be necessary to use multiple pads for additional absorptive capacity. The portion of the second backsheet 29 within line of weakness 40 may be separated and removed from the remainder of the second backsheet 29 creating apertures 45 in first backsheet 26. The sanitary napkin can then be placed onto an additional sanitary napkin such that fluid will flow from the apertures 45 in the first backsheet 26 into the topsheet of the additional sanitary napkin, thereby increasing the overall absorptive capacity.

The topsheet 24 is compliant, soft feeling, and non-irritating to the wearer's skin. Further, the topsheet 24 is liquid pervious permitting liquids (e.g., menses and/or urine) to readily penetrate through its thickness. A suitable topsheet 24 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. A preferred topsheet comprises an apertured formed film. Apertured formed films are preferred for the topsheet because they are pervious to body exudates and yet non-absorbent and have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929,135, issued to Thompson on Dec. 30, 1975; U.S. Pat. No. 4,324,246 issued to Mullane, et al. on Apr. 13, 1982; U.S. Pat. No. 4,342,314 issued to Radel. et al. on Aug. 3, 1982; U.S. Pat. No. 4,463,045 issued to Ahr et al. on Jul. 31, 1984; and U.S. Pat. No. 5,006,394 issued to Baird on Apr. 9, 1991. Each of these patents are incorporated herein by reference. The preferred topsheet for the present invention is the formed film described in one or more of the above patents and marketed on sanitary napkins by The Procter & Gamble Company of Cincinnati, Ohio as "DRI-WEAVE".

In a preferred embodiment of the present invention, the body surface of the formed film topsheet is hydrophilic so as to help liquid to transfer through the topsheet faster than if the body surface was not hydrophilic so as to diminish the likelihood that menstrual fluid will flow off the topsheet rather than flowing into and being absorbed by the absorbent core. In a preferred embodiment, surfactant is incorporated into the polymeric materials of the formed film topsheet such as is described in U.S. patent application Ser. No. 07/794,745, "Absorbent Article Having A Nonwoven and Apertured Film Coversheet" filed on Nov. 19, 1991 by Aziz, et al., which is incorporated herein by reference. Alternatively, the body surface of the topsheet can be made hydrophilic by treating it with a surfactant such as is described in the above referenced U.S. Pat. No. 4,950,254 issued to Osborn, incorporated herein by reference.

In use, the sanitary napkin 20 can be held in place by any support means or attachment means well-known for such purposes. Preferably, the sanitary napkin is placed in the user's undergarment or panty and secured thereto by a fastener such as an adhesive 36. The adhesive 36 provides a means for securing the sanitary napkin in the crotch portion of the panty. Thus, a portion or all of the outer surface of the second backsheet 29 is coated with adhesive. Any adhesive or glue used in the art for such purposes can be used for the adhesive herein, with pressure-sensitive adhesives being preferred. Suitable adhesives are Century A-305-IV manufactured by the Century Adhesives Corporation of Columbus, Ohio; and Instant Lock 34-2823 manufactured by the National Starch and Chemical Company of Bridgewater, N.J. Suitable adhesive fasteners are also described in U.S. Pat. No. 4,917,697. Before the sanitary napkin is placed in use, the pressure-sensitive adhesive is typically covered with a removable release liner 37 in order to keep the adhesive from drying out or adhering to a surface other than the crotch portion of the panty prior to use. Suitable release liners are also described in the above-referenced U.S. Pat. No. 4,917,697. Any commercially available release liners commonly used for such purposes can be utilized herein. Non-limiting examples of suitable release liners are BL30MG-A Silox E1/0 and BL30MG-A Silox 4P/O both of which are manufactured by the Akrosil Corporation of Menasha, Wis. The sanitary napkin 20 of the present invention may be used by removing the release liner 37 and thereafter placing the sanitary napkin in a panty so that the adhesive 36 contacts the panty. The adhesive maintains the sanitary napkin in its position within the panty during use.

In a preferred embodiment of the present invention, the sanitary napkin has two flaps each of which are adjacent to and extend laterally from the side edge of the absorbent core. The flaps are configured to drape over the edges of the wearer's panties in the crotch region so that the flaps are disposed between the edges of the wearer's panties and the thighs. The flaps serve at least two purposes. First, the flaps help serve to prevent soiling of the wearer's body and panties by menstrual fluid, preferably by forming a double wall barrier along the edges of the panty. Second, the flaps are preferably provided with attachment means on their garment surface so that the flaps can be folded back under the panty and attached to the garment facing side of the panty. In this way, the flaps serve to keep the sanitary napkin properly positioned in the panty. The flaps can be constructed of various materials including materials similar to the topsheet, backsheet, tissue, or combination of these materials. Further, the flaps may be a separate element attached to the main body of the napkin or can comprise extensions of the topsheet and backsheet (i.e., unitary). A number of sanitary napkins having flaps suitable or adaptable for use with the sanitary napkins of the present invention are disclosed in U.S. Pat. No. 4,687,478 issued to Van Tilburg on Aug. 18, 1987; U.S. Pat. No. 4,589,876 issued to Van Tilburg on May 20, 1986; is and U.S. Pat. No. 4,608,047, issued to Mattingly on Aug. 26, 1986. Each of these patents are incorporated herein by reference.

In a preferred embodiment of the present invention, an acquisition layer(s) may be positioned between the topsheet and the absorbent core. The acquisition layer may serve several functions including improving wicking of exudates over and into the absorbent core. There are several reasons why the improved wicking of exudates is important, including providing a more even distribution of the exudates throughout the absorbent core and allowing the sanitary napkin 20 to be made relatively thin. (The wicking referred to herein may encompass the transportation of liquids in one, two or all directions (i.e., in the x-y plane and/or in the z-direction). The acquisition layer may be comprised of several different materials including nonwoven or woven webs of synthetic fibers including polyester, polypropylene, or polyethylene; natural fibers including cotton or cellulose; blends of such fibers; or any equivalent materials or combinations of materials. Examples of sanitary napkins having an acquisition layer and a topsheet are more fully described in U.S. Pat. No. 4,950,264 issued to Osborn and U.S. patent application Ser. No. 07/810,774, "Absorbent Article Having Fused Layers", filed Dec. 17, 1991 in the names of Cree, et al. Each of these references are incorporated herein by reference. In a preferred embodiment, the acquisition layer may be joined with the topsheet by any of the conventional means for joining webs together, most preferably by fusion bonds as is more fully described in the above-referenced Cree application.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A sanitary napkin including a topsheet, a first backsheet joined to said topsheet, and an absorbent core positioned between said topsheet and said first backsheet, said first backsheet being initially fluid impervious, said sanitary napkin comprising:

(a) a second backsheet joined to said first backsheet, said second backsheet including a line of weakness defining a portion of said second backsheet to be separated from the remainder of said second backsheet, said second backsheet being secured to said first backsheet within said line of weakness at a plurality of bond sites such that separation of the portion of said second backsheet within said line of weakness form a plurality of apertures in said first backsheet to selectively render said first backsheet fluid pervious, such that said sanitary napkin may be utilized independently to absorb and contain body exudates or may alternatively be utilized in combination with an additional sanitary napkin to absorb and contain body exudates when said apertures provide fluid communication through said first backsheet.

2. The sanitary napkin of claim 1, wherein said line of weakness is substantially continuous.

3. The sanitary napkin of claim 2, wherein said line of weakness includes perforations.

4. The sanitary napkin of claim 1, wherein said second backsheet has a garment facing surface.

5. The sanitary napkin of claim 4, wherein said garment facing surface of said second backsheet includes an adhesive fastening means.

6. The sanitary napkin of claim 5, wherein said sanitary napkin includes a removable release liner to cover said adhesive fastening means.

7. A sanitary napkin including a topsheet, a first backsheet joined to said topsheet, and an absorbent core positioned between said topsheet and said first backsheet, said first backsheet being initially fluid impervious, said sanitary napkin comprising:

(a) a second backsheet joined to said first backsheet, said second backsheet including perforations defining a portion of said second backsheet to be separated from the remainder of said second backsheet, said second backsheet being secured to said first backsheet within said perforations at a plurality of bond sites such that separation of the portion of said second backsheet within said perforations forms a plurality of apertures in said first backsheet to selectively render said first backsheet fluid pervious, such that said sanitary napkin may be utilized independently to absorb and contain body exudates or may alternatively be utilized in combination with an additional sanitary napkin to absorb and contain body exudates when said apertures provide fluid communication through said first backsheet.

8. The sanitary napkin of claim 7, wherein said second backsheet has a garment facing surface.

9. The sanitary napkin of claim 8, wherein said garment facing surface of said second backsheet includes an adhesive fastening means.

10. The sanitary napkin of claim 9, wherein said sanitary napkin includes a removable release liner to cover said adhesive fastening means.

* * * * *